US00PP17645P2

(12) United States Plant Patent
Iwaki et al.

(10) Patent No.: US PP17,645 P2
(45) Date of Patent: Apr. 24, 2007

(54) ***PETUNIA* PLANT NAMED 'SUNSURFGIGABU'**

(50) Latin Name: *Petunia cornuta*
Varietal Denomination: Sunsurfgigabu

(75) Inventors: Kazunari Iwaki, Shiga (JP); Takuro Ishihara, Tokyo (JP); Shinya Miyano, Touosyou-machi (JP)

(73) Assignees: Kesei Rose Nurseries, Inc., Tokyo (JP); Suntory Flowers Ltd., Tokyo (JP)

( * ) Notice: Subject to any disclaimer, the term of this patent is extended or adjusted under 35 U.S.C. 154(b) by 0 days.

(21) Appl. No.: 11/264,779

(22) Filed: Nov. 1, 2005

(51) Int. Cl.
*A01H 5/00* (2006.01)

(52) U.S. Cl. ..... Plt./356

(58) Field of Classification Search ..... Plt./356
See application file for complete search history.

*Primary Examiner*—Kent Bell
(74) *Attorney, Agent, or Firm*—C. A. Whealy

(57) ABSTRACT

A new and distinct cultivar of *Petunia* plant named 'Sunsurfgigabu', characterized by its outwardly spreading, mounded and decumbent plant habit; vigorous and freely branching growth habit; freely flowering habit; large purple violet-colored flowers; long flowering period; and good garden performance.

1 Drawing Sheet

Botanical designation: *Petunia cornuta*.
Cultivar denomination: 'Sunsurfgigabu'.

BACKGROUND OF THE INVENTION

The present Invention relates to a new and distinct cultivar of *Petunia* plant, botanically known as *Petunia cornuta* and hereinafter referred to by the cultivar name Sunsurfgigabu.

The new *Petunia* is a product of a planned breeding program conducted by the Inventors in Higashiomi, Shiga, Japan. The objective of the breeding program is to create new outwardly spreading *Petunias* with large and attractive flowers.

The new *Petunia* originated from a cross-pollination made by the Inventors in August, 2001, of the *Petunia cornuta* Titan Blue, not patented, as the female, or seed, parent with a proprietary selection of *Petunia cornuta* identified as code number 79-200, not patented, as the male, or pollen, parent. The new *Petunia* was selected as a single plant from the resulting progeny of the cross-pollination by the Inventors in a controlled environment in Higashiomi, Shiga, Japan.

Asexual reproduction of the new cultivar by terminal cuttings in a controlled environment in Higashiomi, Shiga, Japan since September, 2003 has shown that the unique features of this new *Petunia* are stable and reproduced true to type in successive generations.

SUMMARY OF THE INVENTION

Plants of the cultivar Sunsurfgigabu have not been observed under all possible environmental conditions. The phenotype may vary somewhat with variations in environment such as temperature and light intensity without, however, any variance in genotype.

The following traits have been repeatedly observed and are determined to be the unique characteristics of 'Sunsurfgigabu'. These characteristics in combination distinguish 'Sunsurfgigabu' as a new and distinct *Petunia* cultivar:

1. Outwardly spreading, mounded and decumbent plant habit.
2. Vigorous and freely branching growth habit.
3. Freely flowering habit.
4. Large purple violet-colored flowers.
5. Long flowering period.
6. Good garden performance.

Plants of the new *Petunia* differ from plants of the female parent, the cultivar Titan Blue, in the following characteristics:

1. Plants of the new *Petunia* are more decumbent than plants of the cultivar Titan Blue.
2. Plants of the new *Petunia* are shorter, but broader than plants of the cultivar Titan Blue.
3. Plants of the new *Petunia* have smaller flowers than plants of the cultivar Titan Blue.

Plants of the new *Petunia* differ from plants of the male parent selection in the following characteristics:

1. Plants of the new *Petunia* are larger than plants of the male parent selection.
2. Plants of the new *Petunia* have larger flowers than plants of the male parent selection.
3. Plants of the new *Petunia* and the male parent selection differ in flower color as plants of the male parent selection have red purple-colored flowers.

Plants of the new *Petunia* can be compared to plants of the cultivar Revolution Violet No. 3, disclosed in U.S. Plant Pat. No. 10,330. In side-by-side comparisons conducted in Higashiomi, Shiga, Japan, plants of the new *Petunia* differed from plants of the cultivar Revolution Violet No. 3 in the following characteristics:

1. Plants of the new *Petunia* were smaller than plants of the cultivar Revolution Violet No. 3.
2. Plants of the new *Petunia* had longer leaves than plants of the cultivar Revolution Violet No. 3.
3. Plants of the new *Petunia* had larger flowers than plants of the cultivar Revolution Violet No. 3.

4. Flowers of plants of the new *Petunia* had more rounded apices than flowers of plants of the new cultivar Revolution Violet No. 3.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Petunia.*

The photograph at the top of the sheet comprises a side perspective view of a typical flowering plant of 'Sunsurfgigabu' grown in a container.

The photograph at the bottom of the sheet comprises a close-up view of typical flowers of 'Sunsurfgigabu'.

DETAILED BOTANICAL DESCRIPTION

The aforementioned photographs and following observations and measurements describe plants grown in Higashiomi, Shiga, Japan, in 15-cm containers for about four months in an outdoor nursery during the early summer with day temperatures about 23° C. and night temperatures about 13° C. Plants were pinched one time. Color references are made to The Royal Horticultural Society Colour Chart, 2001 Edition, except where general terms of ordinary dictionary significance are used.

Botanical classification: *Petunia cornuta* cultivar Sunsurfgigabu.

Parentage:

*Female, or seed, parent.*—*Petunia cornuta* cultivar Titan Blue, not patented.

*Male, or pollen, parent.*—Proprietary selection of *Petunia cornuta* identified as code number 79-200, not patented.

Propagation:

*Type cutting.*—Terminal vegetative cuttings.

*Time to initiate roots.*—About one week at 20° C. to 25° C.

*Time to develop roots.*—About three weeks at 20° C. to 25° C.

*Root description.*—Fine, fibrous, fleshy; light brown in color.

*Rooting habit.*—Freely branching; dense.

Plant description:

*Plant and growth habit.*—Annual flowering plant; indeterminate; outwardly spreading, mounded and decumbent plant habit. Viscid and glandular pubescent. Vigorous growth habit. Freely branching habit with lateral branches developing potentially at every node.

*Plant height.*—About 12.2 cm.

*Plant diameter.*—About 52 cm.

*Lateral branches.*—Length: About 24.6 cm. Diameter: About 2.8 mm. Internode length: About 2.9 cm. Texture: Pubescent. Color: 144A.

*Foliage description.*—Arrangement: Alternate, simple. Length: About 6.7 cm. Width: About 3.6 cm. Shape: Obovate. Apex: Obtuse. Base: Obtuse. Margin: Entire; undulate. Texture, upper and lower surfaces: Pubescent; viscid. Venation pattern: Pinnate; reticulate. Color: Developing foliage, upper surface: 144A. Developing foliage, lower surface: 144B. Fully expanded foliage, upper surface: 137B; venation, close to 144B. Fully expanded foliage, lower surface: 146B; venation, close to 144C. Petiole length: About 7.2 mm. Petiole diameter: About 2.7 mm. Petiole texture, upper and lower surfaces: Viscid. Petiole color, upper and lower surfaces: 144C.

Flower description:

*Flower type and habit.*—Single salverform flowers; flowers face mostly upward or outward; axillary. Flowers not persistent. Freely flowering habit with about 45 flowers and flower buds per plant.

*Natural flowering season.*—Long flowering period, plants flower from spring through late autumn in Japan; flowering continuous during this period.

*Flower longevity on the plant.*—About five days.

*Fragrance.*—Moderate.

*Flower size.*—Diameter: About 8.4 cm. Length: About 4.5 cm. Throat diameter (distal): About 1.5 cm. Tube diameter (proximal): About 3.5 cm.

*Flower buds.*—Length: About 4.7 cm. Diameter: About 9 mm. Shape: Cylindrical. Color: 86B.

*Corolla.*—Quantity/arrangement: Five petals; fused, funnelform. Petal length: About 4 cm.

*Petal width.*—About 3.6 cm.

*Petal shape.*—Very broadly obovate.

*Petal apex.*—Obtuse.

*Petal margin.*—Entire; undulate.

*Petal texture, upper and lower surfaces.*—Smooth; satiny.

*Color.*—Petal, when developing, upper surface: 83A. Petal, when developing, lower surface: 83C. Petal, fully opened, upper surface: N81A; venation, similar to petal color. Petal, fully opened, lower surface: 83C; venation, similar to petal color. Flower throat (inside): 83B; venation, N92C. Flower tube (outside): 79C.

*Sepals.*—Arrangement/appearance: Single whorl of five sepals fused at base, star-shaped calyx. Length: About 2 cm. Width: About 7.4 mm. Shape: Elliptic. Apex: Obtuse. Margin: Entire; undulate. Texture, upper and lower surfaces: Pubescent. Color, upper surface: 137B. Color, lower surface: 144A.

*Peduncles.*—Length: About 2 cm. Width: About 1.6 mm. Strength: Moderately strong. Texture: Pubescent; viscid. Color: 144A.

*Reproductive organs.*—Stamens: Quantity: Five per flower. Anther shape: Ellipsoidal. Anther length: About 2.2 mm. Anther color: 189D. Pollen amount: Moderate. Pollen color: 188A. Pistils: Quantity: One per flower. Pistil length: About 2 cm. Style length: About 1 cm. Style color: About 144D. Stigma shape: Ellipsoidal. Stigma color: 143C. Ovary color: 144A.

*Seed.*—Seed development has not been observed.

Disease/pest resistance: Plants of the new *Petunia* have not been noted to be resistant to specific pathogens and pests common to *Petunia.*

Garden performance: Plants of the new *Petunia* have been observed to have good garden performance and tolerate rain, wind and tolerated temperatures from 0° to 35° C.

It is claimed:

1. A new and distinct cultivar of *Petunia* plant named 'Sunsurfgigabu', as illustrated and described.

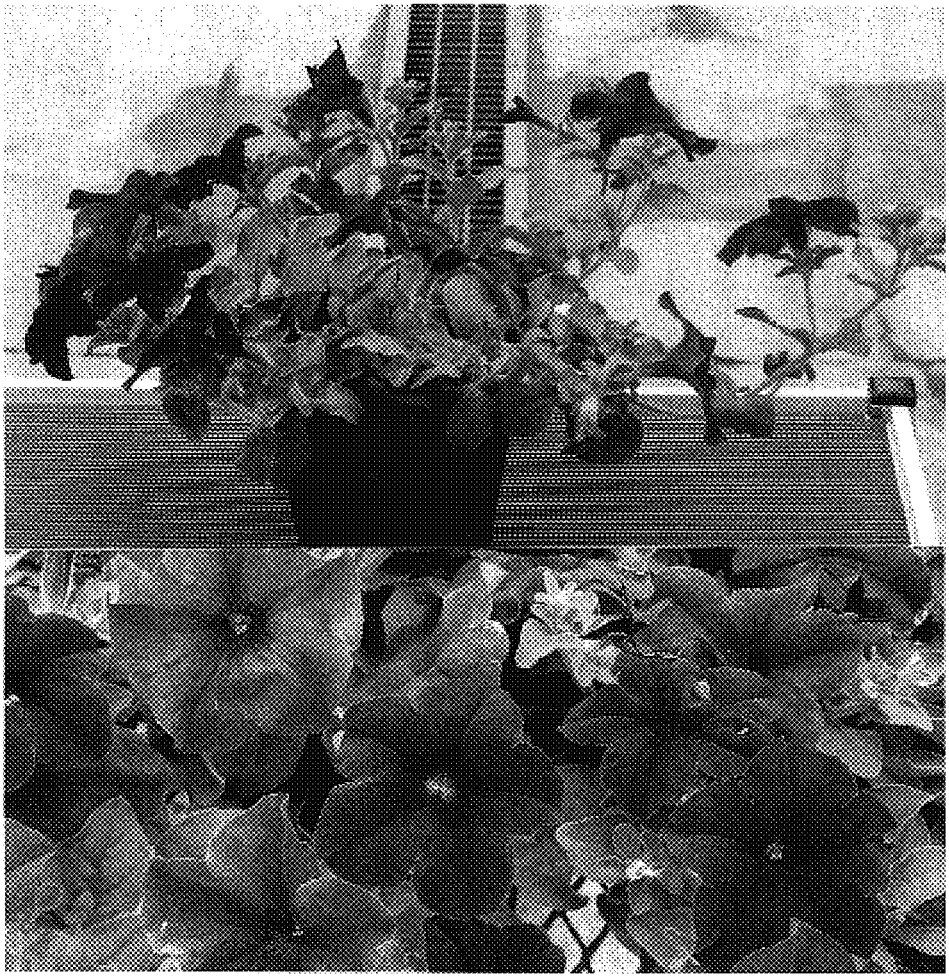

* * * * *